(12) United States Patent
Krapf et al.

(10) Patent No.: US 8,493,076 B2
(45) Date of Patent: Jul. 23, 2013

(54) MEASURING DEVICE

(75) Inventors: Reiner Krapf, Reutlingen (DE); Heiko Braun, Stuttgart (DE); Michael Mahler, Leinfelden-Echterdingen (DE); Christoph Wieland, Stuttgart-Vaihingen (DE); Ulli Hoffmann, Niefern-Oeschelbronn (DE)

(73) Assignee: Robert Bosch GmbH, Stuttgart (DE)

( * ) Notice: Subject to any disclaimer, the term of this patent is extended or adjusted under 35 U.S.C. 154(b) by 1006 days.

(21) Appl. No.: 12/160,451

(22) PCT Filed: Jan. 15, 2007

(86) PCT No.: PCT/EP2007/050322
§ 371 (c)(1),
(2), (4) Date: Jul. 10, 2008

(87) PCT Pub. No.: WO2007/082855
PCT Pub. Date: Jul. 26, 2007

(65) Prior Publication Data
US 2010/0156391 A1    Jun. 24, 2010

(30) Foreign Application Priority Data
Jan. 19, 2006  (DE) .......................... 10 2006 002 666

(51) Int. Cl.
*G01R 27/32*  (2006.01)
(52) U.S. Cl.
USPC .......................................... 324/640; 324/637
(58) Field of Classification Search
USPC ..................... 324/76.19, 637, 640; 342/72
See application file for complete search history.

(56) References Cited

U.S. PATENT DOCUMENTS

| 4,204,833 A | 5/1980 | Kmetz et al. |
| 4,504,833 A | 3/1985 | Fowler et al. |
| 5,357,253 A * | 10/1994 | Van Etten et al. ............... 342/22 |
| 5,867,117 A | 2/1999 | Gogineni et al. |
| 6,344,818 B1 | 2/2002 | Markov |
| 6,784,671 B2 * | 8/2004 | Steele et al. ................... 324/640 |
| 6,967,612 B1 | 11/2005 | Gorman et al. |
| 2005/0179578 A1 | 8/2005 | Healy et al. |
| 2008/0036644 A1 | 2/2008 | Skultety-Betz et al. |

FOREIGN PATENT DOCUMENTS

| CA | 2 318 074 | 7/1999 |
| DE | 199 15 017 | 5/2000 |
| JP | 58-109869 | 6/1983 |
| JP | 2002-181920 | 6/2002 |
| JP | 2006-200766 | 8/2006 |
| WO | 2005/081015 | 9/2005 |
| WO | 2006/003076 | 1/2006 |

* cited by examiner

*Primary Examiner* — Arleen M Vazquez
*Assistant Examiner* — Alesa Allgood
(74) *Attorney, Agent, or Firm* — Michael J. Striker

(57) ABSTRACT

The invention relates to a measuring device comprising a signal unit (20) for emitting a measuring signal (22.1, 22.2) in a measuring frequency range (60, 62, 68, 70) adapted for measurement and an evaluation unit (36) for the spectral evaluation of an evaluation signal (34.1, 34.2) induced by the measuring signal (22.1, 22.2) to a measuring result. According to the invention, the measuring device comprises a signal processing unit (30) adapted to displace a generation signal (26) for generating a measuring signal (22.1, 22.2) in a generation frequency range (48) from the generation frequency range (48) to the measuring frequency range (60, 62, 68, 70).

7 Claims, 4 Drawing Sheets

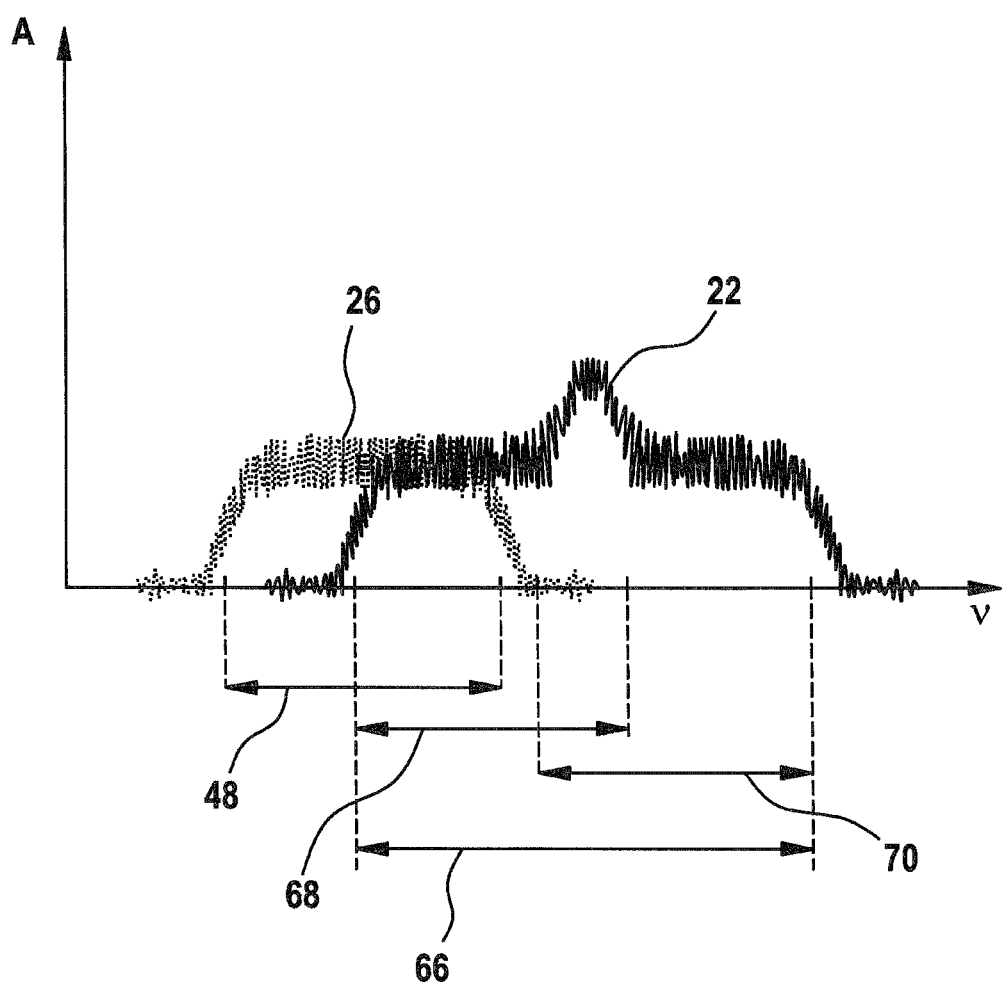

MEASURING DEVICE

CROSS-REFERENCE

The invention described and claimed hereinbelow is also described in PCT/EP2007/050322, filed Jan. 15, 2007 and DE 10 2006 002 666.7, filed Jan. 19, 2006. This German Patent Application, whose subject matter is incorporated here by reference, provides the basis for a claim of priority of invention under 35 U.S.C. 119 (a)-(d).

BACKGROUND OF THE INVENTION

The present invention is directed to a measuring device with a signal unit.

Measuring devices are known that transmit a measurement signal in a certain frequency range in order to perform a measurement, the measurement signal being received and evaluated as an evaluation signal after it interacts with an object to be investigated. In the evaluation, the desired measurement result is ascertained based on a spectral analysis of the measurement signal.

SUMMARY OF THE INVENTION

The present invention is directed to a measuring device with a signal unit for transmitting a measurement signal in a measurement-frequency range that is adapted for a particular measurement, and to an evaluation unit for performing a spectral evaluation of an evaluation signal that was induced by the measurement signal in order to obtain a measurement result.

It is provided that the measuring device includes a signal-processing unit, which is provided to shift a generate signal—which generates the measurement signal and is located in a generation-frequency range—from the generation-frequency range to the measurement-frequency range. As a result, the flexibility of use of the measuring device may be increased in a simple manner. It is possible, in particular, to expand the measurement functionality of existing measuring devices with minimal outlay and in a cost-favorable manner. Existing, cost-favorable signal-generation means may be used to produce the generate signal without their needing to be tailored especially to the measurement-frequency range. A signal located in a frequency range preferably has a signal-to-noise ratio in its frequency spectrum that is greater than one, for each frequency value in the frequency range. This may take place simultaneously for all frequency values in the frequency range, e.g., by generating a pulse. As an alternative, the frequency values in the frequency range may be sampled within a certain time interval, e.g., via frequency modulation of a peak-frequency signal within the frequency range. When the generate signal is shifted, its frequency spectrum may be shifted by a frequency in the frequency scale, with the measurement-frequency range and the generation-frequency range having the same width As an alternative, the generate signal may be shifted to a measurement-frequency range that has a different width, which is broader, in particular. The expression "a measurement-frequency range (of a measurement signal) adapted for a particular measurement" refers, in particular, to a frequency range in which interactions of the measurement signal with the material may be evaluated in order to ascertain a characteristic value that is relevant to the measurement. In addition, a "spectral evaluation" of a signal refers, in particular, to a signal evaluation with which an evaluation result is obtained by ascertaining a characteristic of the signal spectrum. To this end, the course of the signal may be analyzed as a function of the frequency, e.g., by ascertaining a peak position or a peak amplitude. As an alternative or in addition thereto, the course of the signal may be analyzed as a function of time by ascertaining a change in the form of the signal between the time when the signal was transmitted and when it was received. When the measurement signal has a course over time with a certain pattern, e.g., a square or gaussian pattern, a deformation of the pattern caused by an interaction of the measurement signal with a material may be ascertained in the evaluation signal and evaluated. This time-based method is equivalent to the frequency analysis of the signal described above. This is known from Fourier theory and will not be described in greater detail here.

It is also provided that the signal unit is provided for ultra-broadband operation. A good measurement result may therefore be attained with a low spectral energy density. "Ultra-broadband operation" means the use of a frequency range with a band width of at least 500 MHz or at least 15% of the mid-frequency of the frequency range. The mid-frequency is preferably selected in the frequency range of 1 GHz to 15 GHz.

Ultra-broadband operation may be attained by transmitting pulse sequences, by transmitting "pseudo-noise sequences", by using a frequency-modulated, continuous signal, or by using a frequency shift system.

When the evaluation unit is provided for determining a characteristic value for moisture, a greater level of user comfort may be attained. The evaluation unit is preferably provided to determine moisture, in interaction with the signal-processing unit. In particular, the generate signal may be shifted into a measurement-frequency range in which interactions with water molecules of an object under investigation may be evaluated by the evaluation unit in order to determine a moisture level.

In a further embodiment of the present invention, it is provided that the signal-processing unit is provided for shifting the generate signal to at least two measurement-frequency ranges. As a result, a high level of flexibility may be attained in the evaluation of the measurement signal.

Flexible measurement procedures may be attained, in particular, when the measuring device includes at least two measurement modes, which are provided for measuring a characteristic value, and each of which is assigned to one of the measurement-frequency ranges.

When the signal-processing unit is provided to shift the generate signal to the measurement-frequency ranges at least essentially simultaneously, a broad measurement signal that extends across at least two measurement-frequency ranges may be attained.

These measurement ranges may be separated from each other. As a result, certain ranges of the frequency scale may be blocked out, thereby making it possible to prevent an undesired energy distribution of the measurement signal across frequency ranges that are not adapted for a measurement, and to eliminate the need for filtering.

The measurement-frequency ranges advantageously form a continuous measurement-frequency section. As a result, the use of complex expansion methods for expanding the generation-frequency range may be advantageously avoided.

In addition, existing, cost-favorable circuits may be used for the signal-processing unit when they include a modulation unit for modulating the generate signal with at least one modulation signal.

It is furthermore provided that, during operation, the evaluation unit is supplied with a processing signal from the signal-processing unit, which is provided to shift the generate signal.

As a result, components for processing the evaluation signal may be advantageously eliminated.

The measuring device is advantageously designed as a locating device. Objects may therefore be located with a high level of accuracy.

BRIEF DESCRIPTION OF THE DRAWINGS

Further advantages result from the description of the drawing, below. An exemplary embodiment of the present invention is shown in the drawing. The drawing, the description, and the claims contain numerous features in combination. One skilled in the art will also advantageously consider the features individually and combine them to form further reasonable combinations.

FIG. 5 shows a further frequency spectrum of a measurement signal.

DETAILED DESCRIPTION OF THE EXEMPLARY EMBODIMENT

Figure 1:
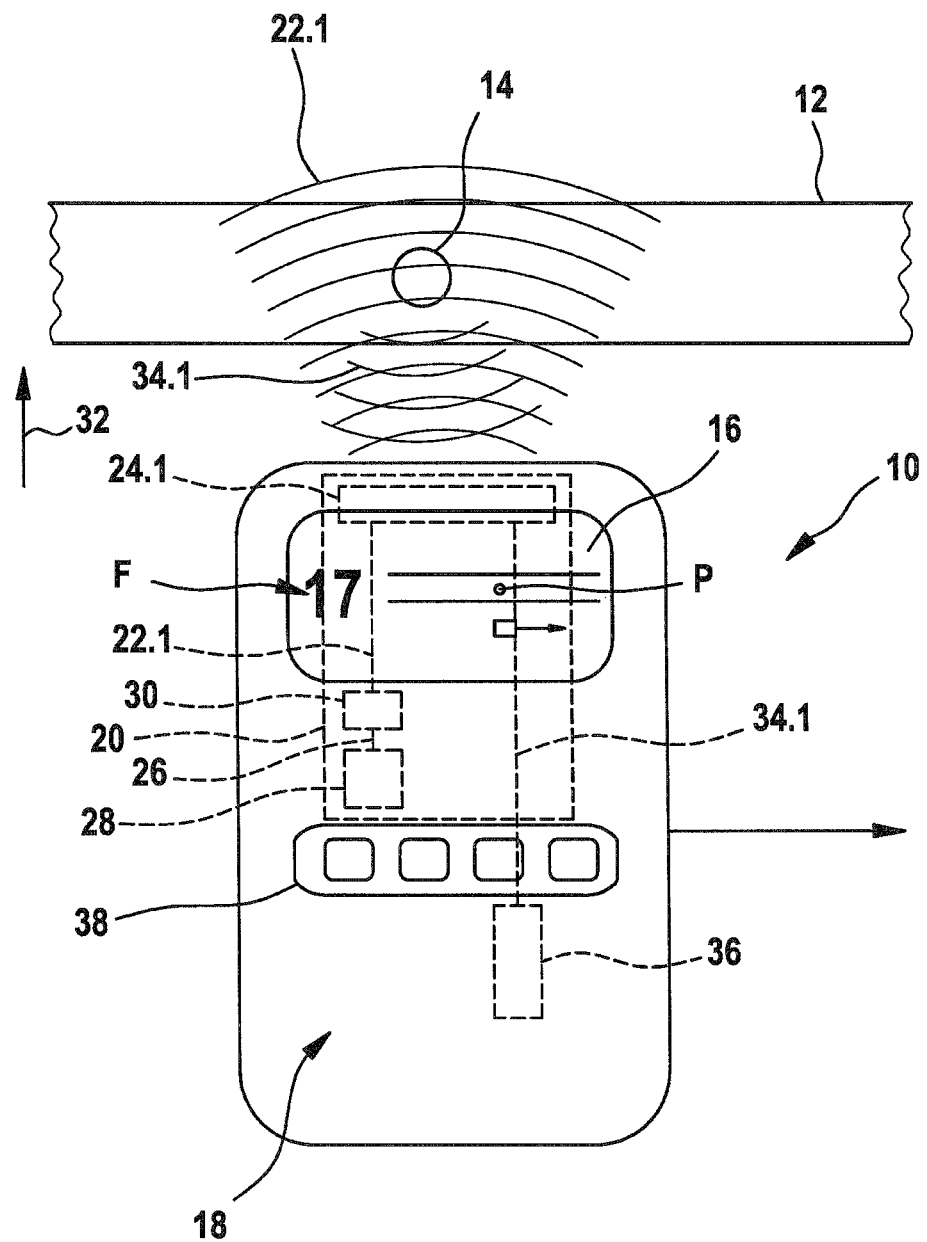
FIG. 1 shows a locating device on a wall.

A measuring device designed as a locating device 10 is shown in FIG. 1. In a first measurement mode, locating device 10 delivers information about objects that are hidden in or behind an object under investigation, e.g., a wall, a floor, a ceiling, etc. These objects are, e.g., water lines, electrical cables, etc. The figure shows a schematic depiction of a wall 12 in which an object 14 of this type is located. Locating device 10, which is moved close to wall 12, enables a user to visualize, in a display 16, the wall 12 being investigated, a characteristic value P depicted as a position of object 14 in wall 12, and the expansion and/or depth of object 14. This is realized using a measuring unit 18, which is provided to determine this information by processing high-frequency signals. To this end, measuring unit 18 includes a signal unit 20, via which high-frequency measurement signals 22.1, 22.2 are generated and coupled into wall 12. To determine characteristic value P of object 14, and to visualize the wall structure, to measurement signals 22.1 and 22.2 are transmitted in two measurement directions 32, 33. Transmission in measurement direction 32 takes place via sensor means 24.1 designed as an antenna element, while measurement signal 22.2 is transmitted via sensor means 24.2, which are also designed as an antenna element. For clarity, FIG. 1 shows only measurement direction 32 and only one sensor means 24.1 (see also FIG. 2). Measurement directions 32, 33 may also be depicted as, e.g., a horizontal direction and a vertical direction. In a further embodiment, it is also feasible that transmission takes place in both measurement directions 32, 33 via sensor means, e.g., sensor means 24.1 designed as an antenna element. It is also feasible that a measurement signal is transmitted in only one direction, e.g., direction 32. In addition, sensor means 24.1, 24.2 may be designed as monostatic and/or bistatic antenna elements.

Transmitted measurement signals 22.1, 22.2 are generated in signal unit 20 via a generate signal 26, which is produced in a signal-generating unit 28 and is processed in a signal-processing unit 30. Measurement signals 22.1, 22.2 excite evaluation signals 34.1, 34.2 in wall 12, which are then received by sensor means 24.1, 24.2.

After measurement signals 22.1, 22.2 are received, they are forwarded to an evaluation unit 36. Evaluation unit 36 evaluates the frequency spectrum of evaluation signals 34.1, 34.2 and obtains measurement results, which are displayed in display 16. Wall 12, characteristic value P of object 14, locating device 10 itself, and its direction of motion relative to wall 12 are shown in display 16.

Figure 2:
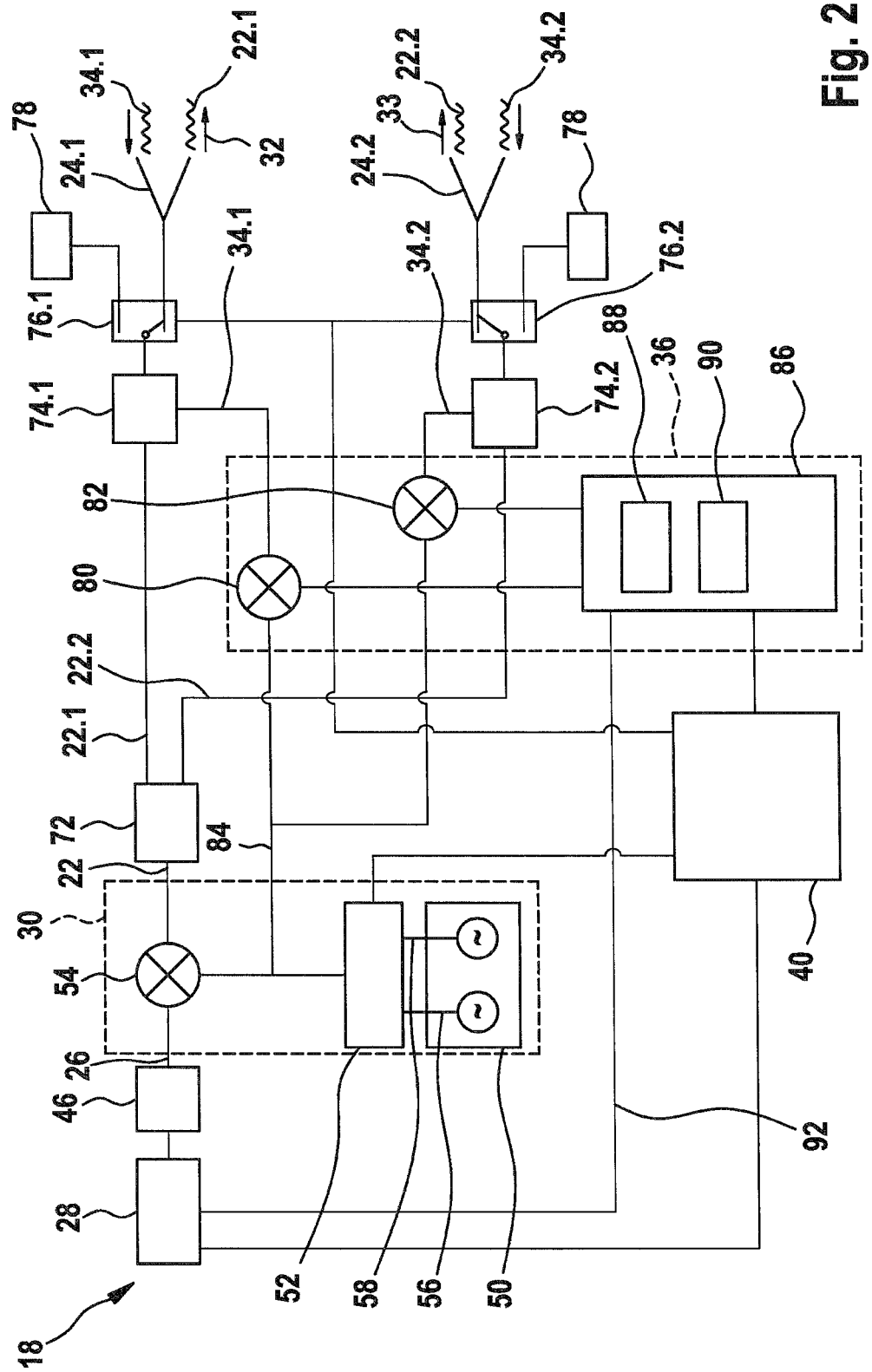
FIG. 2 shows a measuring unit of the locating device in FIG. 1, in a schematicized depiction, FIG. 3 a broadband signal plotted as amplitude versus time.

In a second measurement mode, the operator may also be informed of a characteristic value F, which represents the moisture content of wall 12. To this end, generate signal 26 is processed in signal-processing unit 30 such that measurement signals 22.1, 22.2 are adapted for a measurement of characteristic value F in wall 12. The design and mode of operation of signal-processing unit 30 are illustrated in FIG. 2. The operator may select various measurement procedures via a control unit 38, e.g., measurement procedures in which only the first measurement mode is activated, i.e., determining the location of object 14, measurement procedures in which only the second measurement mode is activated, i.e., determining characteristic value F, or measurement procedures in which both measurement modes are activated. As an alternative or in addition thereto, a graph of moisture in wall 12 may be ascertained in this second measurement mode.

A schematic depiction of measuring unit 18 is shown in FIG. 2. The description in this section also refers to FIGS. 3 through 5. Of the elements depicted in FIG. 1, the following are shown: Signal-generation unit 28, signal-processing unit 30, sensor means 24.1, 24.2 of signal unit 20, and evaluation unit 36.

It is assumed that the operator of control unit 38 selects a measuring procedure in which the first and second measurement modes are carried out. With the first measurement mode, the aim, in particular, is to detect a certain type of plastic of which object 14 is made, in order to locate object 14. With the second measurement mode, the aim is to determine characteristic value F of wall 12.

Figure 3:
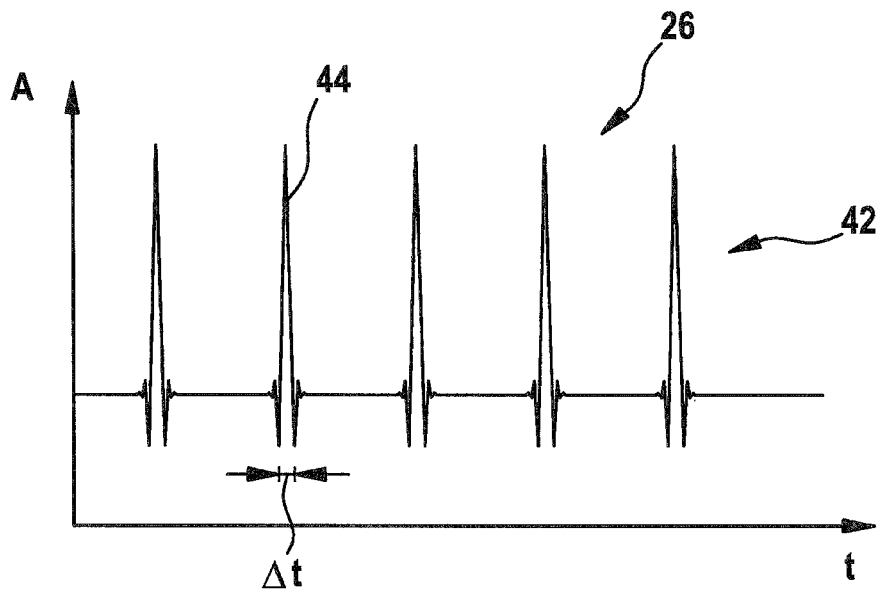

First, signal-generation unit 28, which is designed as an SR diode (step recovery diode), is put into operation by a control unit 40. Generate signal 26, which is designed as an UWB (ultra-wide band) signal and is produced by signal-generation unit 28, is shown in FIG. 3 as a plot of amplitude versus time. The plot shows a sequence 42 of pulses 44. Pulses 44 are generated with a pulse duration Δt of 0.5 ns and occur in regular succession. It is also feasible to use a transistor or a transistor circuit to generate pulses 44. A time interval between two directly successive pulses 44, which is selected to be constant in this exemplary embodiment, may also be designed as a random variable. The sequence may be designed, e.g., as a PN (pseudo-noise) sequence. As an alternative to the generation of pulses 44, generate signal 26 may also be produced as a frequency-modulated, continuous signal (FMCW—frequency-modulated continuous wave).

After generate signal 26 is created, it is sent to a filter 46. After it is filtered, generate signal 26 has the frequency spectrum shown in FIG. 4 as a plot of amplitude versus frequency. Generate signal 26 has a mid-frequency $v_{EM}$ of 5 GHz and extends across a generation-frequency range 48 that corresponds to a bandwidth Δv of 2 GHz around mid-frequency $v_{EM}$. A lower frequency is $v_{EU}$=1 GHz and an upper frequency of generation-frequency range 48 is $v_{EO}$=3 GHz. All of the frequency values described here are examples. Further frequency values are also feasible, of course.

Generate signal 26 is then sent to signal-processing unit 30. It is designed as a modulation unit that includes a signal-generation unit 50, a switching device 52, and a mixing unit 54. Signal-generation unit 50 is designed as a dielectric oscillator and generates two processing signals 56, 58, which have a frequency $f_1=4$ GHz or $f_2=6.5$ GHz, and which are sent to switching device 52. As an alternative, signal-generation unit 50 may be designed as a voltage-controlled oscillator (VCO), an oscillating circuit, a variable capacitance diode with quartz, or as a digital circuit, e.g., a FPGA (field-programmable gate array). Via switching device 52, one of the processing signals 56, 58 may be designed as a modulation signal for modulating generate signal 26, or generate signal 26 may be processed with both processing signals 56, 58, which are designed as modulation signals. It is feasible for generate signal 26 to be processed with more than two processing signals. In this exemplary embodiment, processing signal 56 or 58 is assigned to the first or second measurement mode.

Figure 4:
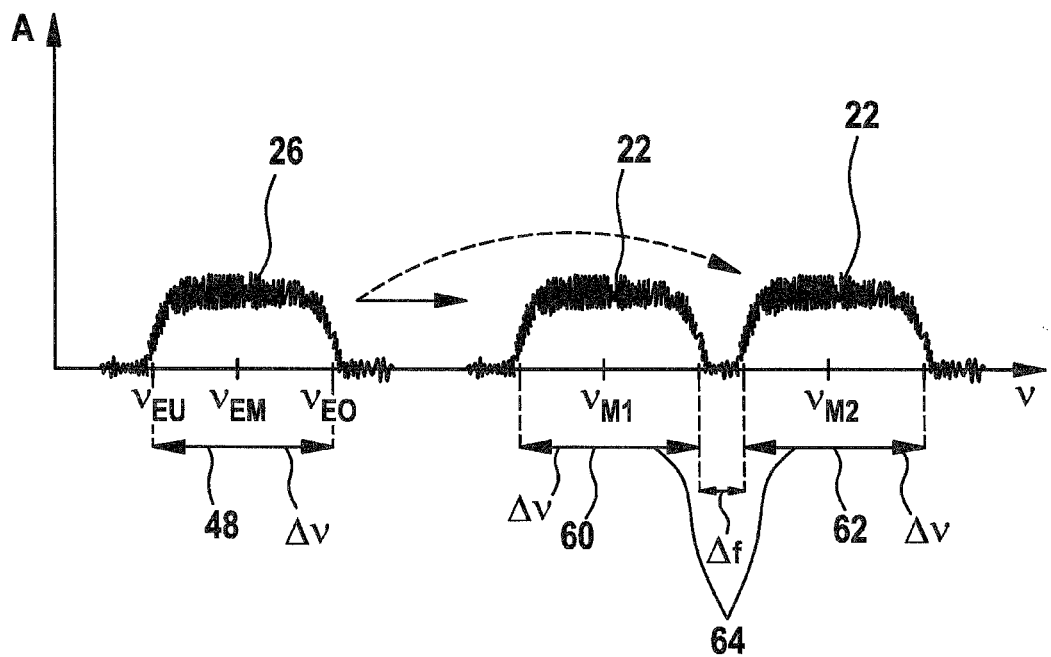
FIG. 4 shows frequency spectra of measurement signals that have been shifted into two measurement-frequency ranges.

In the first measurement mode, processing signal 56 is sent to mixing unit 54, and generate signal 26 is thereby shifted from generation-frequency range 48 to a first measurement-frequency range 60. This is depicted in FIG. 4 as a solid arrow. Generate signal 26, which is shifted to first measurement-frequency range 60, is a measurement signal 22 that is divided and then transmitted as measurement signal 22.1, 22.2. Generate signal 26 is shifted with frequency $f_1$ when processed. Measurement signal 22 therefore has a mid-frequency $v_{M1}$ of 6 GHz and extends across first measurement-frequency range 60 with bandwidth $\Delta v=2$ GHz. First measurement-frequency range 60 is selected such that measurement signals 22.1, 22.2 coupled into wall 12 interact with molecules of the plastic to be detected, thereby making it possible to perform an evaluation based on the frequency spectrum of evaluation signals 34.1, 34.2 in order to determine position P of object 14. After the first measurement mode has been carried out, switching device 52 is controlled by control unit 40, and processing signal 58 is sent to mixing unit 54, thereby shifting generate signal 26 from generation-frequency range 48 to a second measurement-frequency range 62. This is indicated by a dashed arrow. Measurement signal 22 generated as a result has a mid-frequency $v_{M2}$ of 8.5 GHz and extends across second measurement-frequency range 62, also with bandwidth $\Delta v=2$ GHz. Second measurement-frequency range 62 is tuned such that measurement signals 22.1, 22.2 interact with water molecules in wall 12, thereby making it possible to determine characteristic value F by performing a spectral evaluation of related evaluation signals 34.1, 34.2.

Locating device 10 is designed to perform a further measuring procedure, with which generate signal 26 is shifted simultaneously from generation-frequency range 48 into two measurement-frequency ranges. In a first example, generate signal 26 is shifted simultaneously to measurement frequency ranges 60, 62 by switching device 52 sending both processing signals 56, 58 to mixing unit 54. As an alternative, signal-processing unit 30 may include two modulation units, which may serve to modulate generate signal 26 with a processing signal. They may be connected in series, in which case generate signal 26 is modulated successively, or they may be connected in parallel, in which case generate signal 26 is divided into two partial signals, each of which is modulated by a processing signal. The partial signals are combined with each other after they are modulated. Via the selection of the processing signals, a measurement-frequency section of the frequency scale that is tailored to a certain measurement may be attained easily and with great flexibility. A measurement-frequency section 64 of measurement-frequency ranges 60, 62, which are separated from each other, are depicted in this example and in the example shown in FIG. 4. As a result, it is possible, in particular, to specifically eliminate intervals in the frequency scale—e.g., interval $\Delta f$ in this case—which are not adapted for a measurement, thereby avoiding the use of a signal filter and realizing a particularly effective use of the signal output.

A continuous measurement-frequency section 66 of two overlapping measurement-frequency ranges 68, 70 is depicted in a further example, and in the example shown in FIG. 5, in which generate signal 26 (shown as a dashed line in the figure) is shifted simultaneously by signal-processing unit 30. As a result, a broad interval of the frequency scale for a measurement may be easily attained without the need to use complex methods to expand generation-frequency range 48. In a further example, generate signal 26—which has not been shifted—may represent measurement signal 22, in that signal-processing unit 30 is switched off, or generate signal 26 is modulated with a constant processing signal.

After processing, measurement signal 22 is sent to a signal divider 72, in which it is divided into two measurement signals 22.1, 22.2. After they are divided, measurement signals 22.1, 22.2 have essentially the same signal output, which is equal to half the output of measurement signal 22. An alternative division of the signal output of measurement signal 22 into measurement signals 22.1, 22.2 is also feasible. While they are being divided, it is also possible for one of the measurement signals 22.1 or 22.2 to be phase-shifted relative to the other measurement signal 22.2 or 22.1. Measurement signals 22.1, 22.2 are then sent via a signal-dividing unit 74.1 or 74.2 to a switching device 76.1 or 76.2. Via switching device 76.1 or 76.2, which is controllable by control unit 40, measurement signal 22.1 or 22.2 may be sent to a reference circuit 78 for calibrating locating device 10, or it may be sent to sensor element 24.1 or 24.2 for transmission in a measurement direction 32 or 33. Measurement signals 22.1, 22.2, which are transmitted by sensor elements 24.1, 24.2 in the form of electromagnetic radiation, have different polarization directions. It is also feasible that signal unit 20 includes sensor means for each measurement-frequency range, e.g., measurement-frequency ranges 60, 62 of measurement signal 22.

Measurement signals 22.1, 22.2 excite evaluation signals 34.1, 34.2, which are received by sensor elements 24.1, 24.2. Evaluation signals 34.1, 34.2 are separated from measurement signals 22.1, 22.2 in signal-dividing unit 74.1 or 74.2, which is designed as a circulator, and they are transmitted to evaluation unit 36. Evaluation unit 36 includes two modulation units 80, 82, for demodulating evaluation signals 34.1, 34.2.

Modulation units 80, 82 are connected with signal-processing unit 30. At least one processing signal is sent via a line 84 to modulation units 80, 82. Processing signal, e.g., processing signal 56 and/or processing signal 58, is used to process generate signal 26. After demodulation, evaluation signals 34.1, 34.2 are sent to a signal-processing device 86. It includes an analog-digital converter 88 and a data-processing unit 90, which is provided for performing a spectral evaluation of evaluation signals 34.1, 34.2. It is designed, e.g., as a digital signal processing (DSP) unit. Before digital conversion, the mean of evaluation signals 34.1, 34.2 may be calculated, as an option, thereby making it possible to increase the signal-to-noise ratio.

When a PN sequence is generated for generate signal 26, it is possible, as an option, to correlate evaluation signals 34.1, 34.2 with a reference signal 92 in signal-processing device 86. The result of the correlation is then sampled and run through an analog/digital conversion. Before this conversion, the mean of evaluation signals 34.1, 34.2 may be calculated, and/or high-frequency components may be filtered. Generate signal 26 is used as reference signal 92 in this exemplary embodiment. Measurement signal 22 may be used as an alternative. In a further variant, after analog/digital conversion, evaluation signals 34.1, 34.2 may be correlated with reference signal 92, e.g., in data-processing unit 90. It is feasible to use digital filters before correlation, thereby making it possible to improve a measurement result. After evaluation signals 34.1, 34.2 are evaluated, evaluation results are sent to display 16 (FIG. 1), where they are displayed. In a further embodiment of locating device 10, it is also possible—in order to expand the functionalities available for detecting hidden objects—to use further measuring units, which are based on inductive and/or capacitive methods, in addition to measuring unit 18. A user could switch between these measuring units and measuring unit 18 manually or automatically.

What is claimed is:

1. A locating device for locating objects, comprising:
   a signal unit for transmitting a measurement signal with a measurement-frequency range, wherein the signal unit is configured for ultra-broadband operation;
   an evaluation unit for performing the spectral evaluation of an evaluation signal induced by the measurement result;
   a signal-processing unit for shifting a generate signal with a generation-frequency range from said generation-frequency range to the measurement-frequency range, wherein said generate signal generates the measurement signal, wherein the signal-processing unit is configured to shift the generate signal to at least measurement-frequency ranges; and
   at least two measurement modes configured for measuring a characteristic value, and each of which is assigned to one of the measurement-frequency ranges.

2. The locating device as recited in claim 1, wherein the evaluation unit is provided for determining a characteristic value of moisture.

3. The locating device as recited in claim 1, wherein the signal-processing unit is provided to shift the generate signal to the measurement-frequency ranges at least essentially simultaneously.

4. The locating device as recited in claim 1, wherein the measurement-frequency ranges from a continuos measurement-frequency section.

5. The locating device as recited in claim 1, wherein the signal-processing unit includes a modulation unit for modulating the generate signal with at least one modulation signal.

6. The locating device as recited in claim 1, wherein the evaluation unit is supplied, during operation, with a processing signal from the signal-processing unit, which is provided to shift the generate signal.

7. A method for operating a measuring device, comprising the following steps:
   providing a signal unit, wherein the signal unit is configured for ultra-broadband operation;
   transmitting a measurement signal with a measurement-frequency range using the signal unit;
   providing an evaluation unit;
   performing a spectral evaluation of an evaluation signal induced by the measurement signal in order to obtain a measurement result;
   providing a signal-processing unit;
   shifting a generate signal with a generation-frequency range from said generation-frequency range to the measurement-frequency range using said signal-processing unit, wherein said generate signal generates the measurement signal, and wherein the signal-processing unit shifts the generate signal to at least two measurement-frequency ranges; and
   measuring a characteristic value using said at least two measurement modes, wherein each of said at least two measurement modes is assigned to one of the measurement-frequency ranges.

* * * * *